United States Patent [19]

Ife

[11] Patent Number: 4,547,506

[45] Date of Patent: Oct. 15, 1985

[54] 2-PYRIDYLAMINOAKYLAMINO-4-PYRIMI-DONES USEFUL AS HISTAMINE $H_1$-ANTAGONISTS

[75] Inventor: Robert J. Ife, Stevenage, England

[73] Assignee: Smith Kline & French Laboratories Limited, Welwyn Garden City, England

[21] Appl. No.: 563,495

[22] Filed: Dec. 20, 1983

[30] Foreign Application Priority Data

Dec. 23, 1982 [GB] United Kingdom ................ 8236638

[51] Int. Cl.$^4$ .................. A61K 31/505; C07D 239/02
[52] U.S. Cl. ..................... 514/272; 544/320; 544/321; 546/256; 546/295; 546/296
[58] Field of Search ............... 544/320, 321; 424/251; 546/295, 296; 514/272

[56] References Cited

U.S. PATENT DOCUMENTS

| | | | |
|---|---|---|---|
| 3,535,328 | 10/1970 | Zielinski | 546/275 |
| 3,932,644 | 1/1976 | Durant et al. | 424/263 |
| 4,154,834 | 5/1979 | Brown et al. | 424/251 |
| 4,218,452 | 8/1980 | Brown et al. | 544/321 |
| 4,227,000 | 10/1980 | Brown | 544/321 |
| 4,255,428 | 3/1981 | Brown et al. | 544/320 |

OTHER PUBLICATIONS

Kaldrikyan et al, Chem. Abst. 78:124533f (1973).
Batzri et al, Chem. Abst. 100:29483d (1984).
Teikoku Hormone Mfg. Co. Ltd. Chem. Abst. 100:191885h (1984).
Kitteringham et al, Chem. Abst. 101:7191a (1984).
Burger, Medicinal Chemistry, 2nd Edition, pp. 42–43.
Bertaccini et al, Chem. Abst. 100:61607h.
Batzri et al, Chem. Abst. 100:29483d.

*Primary Examiner*—Robert Gerstl
*Assistant Examiner*—Cecilia Shen
*Attorney, Agent, or Firm*—Joan S. Keps; Richard D. Foggio; Alan D. Lourie

[57] ABSTRACT

Pyridine derivatives are disclosed which are useful as histamine $H_1$-antagonists.

15 Claims, No Drawings

2-PYRIDYLAMINOAKYLAMINO-4-PYRIMIDONES USEFUL AS HISTAMINE H₁-ANTAGONISTS

This invention relates to certain pyridine derivatives, a process for their preparation, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines") histamine $H_1$-antagonists) a common example of which is mepyramine.

According to the present invention there is provided compounds of formula (1):

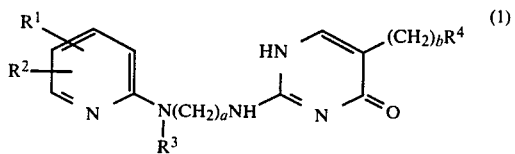

and pharmaceutically acceptable salts thereof where
$R^1$ and $R^2$ are the same or different and are hydrogen, $C_{1-6}$ alkyl, $C_{1-6}$ alkoxy, or halogen;
$R^3$ is $C_{1-6}$ alkyl, $C_{3-8}$ cycloalkyl $C_{1-6}$ alkyl, optionally substituted phenyl or optionally substituted phenyl $C_{1-6}$ alkyl, where the optional substituents are one or more $C_{1-6}$ alkyl, $C_{1-6}$ alkoxy, halogen, or hydroxy groups; or is optionally substituted pyridyl or optionally substituted pyridyl $C_{1-6}$ alkyl where the optional substituents are one or more $C_{1-6}$ alkyl or $C_{1-6}$ alkoxy groups or halogen atoms;
a is from 2 to 4
b is from 1 to 6 $R^4$ is hydrogen, optionally substituted phenyl where the optional substituents are one or more $C_{1-6}$ alkyl, $C_{1-6}$ alkoxy, nitro or hydroxy groups or halogen atoms, or a methylenedioxy group, or is an optionally substituted pyridyl group where the optional substituents are one or more $C_{1-6}$ alkyl, $C_{1-6}$ alkoxy groups or halogen atoms; or is a $C_{3-8}$ cycloalkyl group; or is N-oxo-3-pyridyl; N-oxo-6-methyl-3-pyridyl; 6-hydroxymethyl-3-pyridyl; N-oxo-4,6-dimethyl-3-pyridyl; 6-hydroxymethyl-4-methyl-3-pyridyl; N-oxo-5,6-dimethyl-3-pyridyl; 6-hydroxymethyl-5-methyl-3-pyridyl; or N-oxo-4-pyridyl, or is a pyridone group in which the nitrogen atom is optionally substituted with $C_{1-6}$ alkyl.

Examples of $C_{1-6}$ alkyl groups for $R^1$, $R^2$ and $R^3$ are methyl, ethyl and n-propyl.

Examples of $C_{1-6}$ alkoxy groups for $R^1$ and $R^2$ are methoxy, ethoxy and n-propoxy.

Examples of halogens for $R^1$ and $R^2$ are fluorine, chlorine and bromine.

$R^1$ can be hydrogen, halogen, particularly bromine or $C_{1-6}$ alkyl, particularly methyl.

Preferably $R^2$ is hydrogen.

Most preferably $R^1$ and $R^2$ are both hydrogen.

Preferably a is 3 or 4.

When $R^3$ is $C_{1-6}$ alkyl, it can be methyl or propyl.

When $R^3$ is an optionally substituted phenyl or phenyl $C_{1-6}$ alkyl or is pyridyl or pyridyl $C_{1-6}$ alkyl, preferably the phenyl or pyridyl moiety contains a maximum of two substituents.

When $R^4$ is an optionally substituted phenyl group, preferably it contains a maximum of two substituents or a methylenedioxy group. When $R^4$ is pyridyl preferably it contains a maximum of two substituents.

Examples of $C_{1-6}$ alkyl substituents for the optionally substituted phenyl, the optionally substituted pyridyl and the optionally substituted phenyl- and pyridyl $C_{1-6}$ alkyl groups for $R^3$, the optionally substituted phenyl and optionally substituted pyridyl groups for $R^4$ and the optional substituent for the pyridone group for $R^4$ are methyl and ethyl.

Examples of $C_{1-6}$ alkoxy substituents for the optionally substituted phenyl, the optionally substituted pyridyl and the optionally substituted phenyl- and pyridyl $C_{1-6}$ alkyl groups for $R^3$, and the optionally substituted phenyl and optionally substituted pyridyl groups for $R^4$ are methoxy and ethoxy.

Examples of halogen substituents for the optionally substituted phenyl, the optionally substituted pyridyl and the optionally substituted phenyl- and pyridyl $C_{1-6}$ alkyl groups $R^3$ are fluorine, chlorine and bromine.

Examples of halogen substituents for the optionally substituted phenyl and pyridyl groups $R^4$ are fluorine, chlorine and bromine.

Examples of optionally substituted phenyl groups for $R^3$ and for the phenyl moiety of a phenyl $C_{1-6}$ alkyl group for $R^3$ are phenyl, 2-chlorophenyl, 3-chlorophenyl, 4-chlorophenyl, 4-fluorophenyl, 4-bromophenyl, 4-hydroxyphenyl, 4-methoxyphenyl or 4-methylphenyl. When $R^3$ is an optionally substituted pyridyl or pyridyl $C_{1-6}$ alkyl group it can be an optionally substituted 2-, 3- and 4-pyridyl group.

Examples of substituted pyridyl groups and the pyridyl moiety of the pyridyl $C_{1-6}$ alkyl group for $R^3$ are 5-fluoro-2-pyridyl, 5-chloro-2-pyridyl and 5-bromo-2-pyridyl.

Examples of $C_{3-8}$ cycloalkyl $C_{1-6}$ alkyl groups for $R^3$ are cyclopentylmethyl and cyclohexylmethyl.

By way of example b can be 1, 2 or 3. Preferably it is 1.

Examples of optionally substituted phenyl groups for $R^4$ are phenyl, 2-chlorophenyl, 3-chlorophenyl, 4-chlorophenyl, 3,4-dichlorophenyl, 2-bromophenyl, 3-bromophenyl, 4-bromophenyl, 4-fluorophenyl, 4-methylphenyl, 4-methoxyphenyl, b 4-hydroxyphenyl, 3-nitro-4-hydroxyphenyl and 3,4-methylenedioxy phenyl.

When the phenyl group $R^4$ is substituted, preferably the substituent is in position 3 and/or 4 relative to the point of attachment at the $(CH_2)_b$ group.

Examples of optionally substituted pyridyl groups for $R^4$ are 2-pyridyl, 5-fluoro-2-pyridyl, 5-chloro-2-pyridyl and 5-bromo-2-pyridyl, 3-pyridyl, 4,6-dimethyl-3-pyridyl, 5,6-dimethyl-3-pyridyl, 4-pyridyl and in particular 6-methyl-3-pyridyl.

Examples of $C_{3-8}$ cycloalkyl groups for $R^4$ are cyclopentyl and cyclohexyl.

The pyridone group $R^4$ has a number of isomers (a) to (f) below:

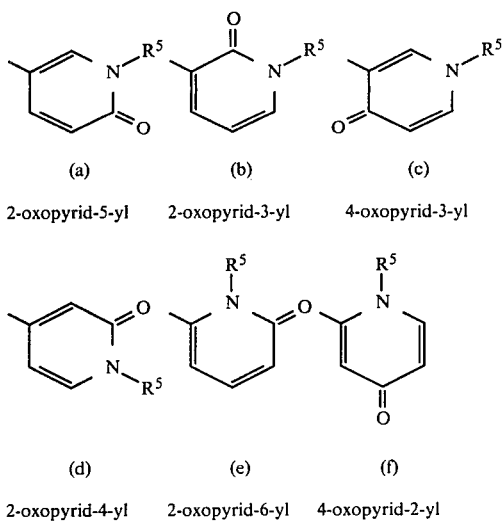

(a) 2-oxopyrid-5-yl  (b) 2-oxopyrid-3-yl  (c) 4-oxopyrid-3-yl (d) 2-oxopyrid-4-yl  (e) 2-oxopyrid-6-yl  (f) 4-oxopyrid-2-yl where $R^5$ is hydrogen or a $C_{1-6}$ alkyl group. Accordingly reference to pyridone is to be understood to incude reference to all these isomers unless the context requires otherwise.

When $R^5$ is hydrogen, the pyridone group can also exist as an enol tautomer. This keto-enol tautomerism is represented by the partial structures below:

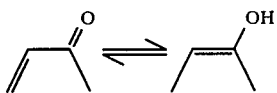

So by way of example isomer (d) can exist in two tautomeric forms as follows:

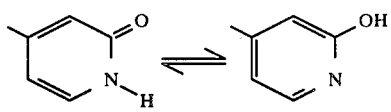

Preferably the group $R^4$ is an isomer of formula (d).

The compounds of formula (1) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

Compounds of formula (1) can be made by reacting a compound of formula (2):

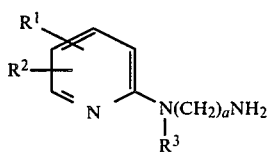

where $R^1$, $R^2$, $R^3$ and a are as defined with reference to formula (1) (where any hydroxy group in $R^3$ is optionally protected);
with a compound of formula (3):

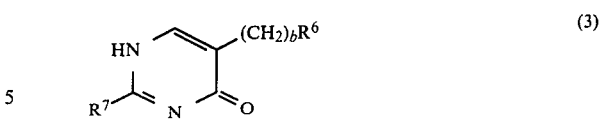

where
$R^6$ is hydrogen, optionally substituted phenyl where the optional substituents are one or more $C_{1-6}$ alkyl, $C_{1-6}$ alkoxy, nitro or optionally protected hydroxy groups or halogen atoms, or a methylenedioxy group, or is an optionally substituted pyridyl group where the optional substituents are one or more $C_{1-6}$ alkyl or $C_{1-6}$ alkoxy groups or halogen atoms; or is a $C_{3-8}$ cycloalkyl group, or is N-oxo-3-pyridyl; N-oxo-6-methyl-3-pyridyl; N-oxo-4,6-dimethyl-3-pyridyl; N-oxo-5,6-dimethyl-3-pyridyl; or N-oxo-4-pyridyl, or is a pyridine group substituted with a protected hydroxy group or a pyridone group in which the nitrogen atom is substituted with $C_{1-6}$ alkyl; b is as defined with reference to formula (1); $R^7$ is a group displaceable with amine and thereafter removing any hydroxy protecting groups; optionally converting the compound of formula (1) so obtained where $R^4$ is N-oxo-6-methyl-3-pyridyl; N-oxo-4,6-dimethyl-3-pyridyl; N-oxo-5,6-dimethyl-3-pyridyl; into the corresponding compound of formula (1) where $R^4$ is 6-hydroxymethyl-3-pyridyl; 6-hydroxymethyl-4-methyl-3-pyridyl; or 6-hydroxymethyl-5-methyl-3-pyridyl; where $R^4$ in the product so obtained is 4-hydroxyphenyl optionally converting it into 4-hydroxy-3-nitrophenyl; and thereafter optionally converting the compound of formula (1) so obtained into a salt.

The compounds of formula (1) where $R^4$ is N-oxo-6-methyl-3-pyridyl; N-oxo-4,6-dimethyl-3-pyridyl; or N-oxo-5,6-dimethyl-3-pyridyl can be converted into the corresponding compound of formula (1) where $R^4$ is 6-hydroxymethyl-3-pyridyl; 6-hydroxymethyl-4-methyl-3-pyridyl; or 6-hydroxymethyl-5-methyl-3-pyridyl; by reacting with an organic anhydride for example trifluoroacetic anhydride.

Examples of hydroxy protecting groups are methoxymethyl, methylthiomethyl, tetrahydropyranyl, arylmethyl, for example benzyl, $C_{1-6}$ alkyl, for example methyl, and alkanoyl, for example formyl or acetyl.

These protecting groups can be removed by standard methods, for example where the protecting group is $C_{1-6}$ alkanoyl or $C_{1-6}$ alkyl, by acid or basic hydrolysis.

Pharmaceutically acceptable salts of compounds of formula (1) can be prepared by standard methods, for example by reacting a solution of the compound of formula (1) with a solution of the acid.

The use of protecting groups is discussed in J. F. McOmie, Protective Groups in Organic Chemistry, 1973, Plenum Press, IBSN 0-306-30717-0.

Examples of groups $R^7$ are C alkylthio (particularly methylthio), benzylthio, chlorine, bromine and nitroamino. Preferably $R^7$ is nitroamino.

This reaction can be carried out at an elevated temperature in the absence of a solvent, for example at from 80° to 170°, preferably from 120° to 140°, or in a solvent at an elevated temperature, for example at the reflux temperature of the reaction mixture. The choice of solvent is affected by solubility characteristics of the reactants. Preferably the solvent is pyridine, a picoline or mixture of picolines, a $C_{1-6}$ alkanol, preferably ethanol or 1-propanol, 1,2-ethanediol, a high boiling alkoxyaryl ether for example anisole, or a polar aprotic solvent, for example dimethylformamide, dimethylacetamide, dimethylsulphoxide, hexamethylphosphoramide or sulpholane.

Compounds of formula (2) can be prepared by reacting a compound of formula (4):

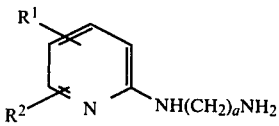

where $R^1$ and $R^2$ and a are as defined with reference to formula (1), with a compound of formula (5):

where $R^3$ is as defined with reference to formula (2) and where any hydroxy group is protected and X is halogen in the presence of a strong base.

Examples of hydroxy protecting groups for $R^3$ are discussed previously. These protecting groups can be introduced by standard methods.

Compounds of formula (4) can be prepared in turn by reacting a compound of formula (6):

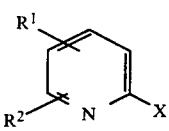

where $R^1$ and $R^2$ are as defined with reference to formula (1) and X is halogen with an amine of formula (7)

Compounds of formula (2) can also be prepared by reacting a compound of formula (8):

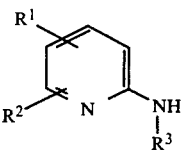

$R^1$, $R^2$ and $R^3$ are as defined with reference to formula (2) where any hydroxy groups are protected with a compound of formula (9)

where a is as defined with reference to formula (1), X is halogen, $R^8$ is a protected amino group in the presence of a strong base and thereafter removing the protecting group.

Examples of protected amino groups for $R^8$ include phthalimido. In formula (5), (6) and (9) X can be chlorine, bromine or iodine.

Examples of strong bases are alkali metal hydrides, particularly sodium hydride. The reaction is carried out in the presence of a polar solvent for example dimethylsulphoxide.

The protected amino group can be converted into amino by standard methods, for example when it is phthalimido by reaction with concentrated hydrochloric acid or hydrazine.

Compounds of formula (3) are known or can be made by known methods as described in for example U.S. Pat. Nos. 4,145,546, 4,154,834, European Patent Specification No. 17679 and European Patent Specification No. 0068833.

Compounds of formulae (5) to (9) are known or can be made by known methods.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of the Examples have pA values greater than 6.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier of parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol.

Where appropriate, bronchodilators and antiasthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included.

Each dosage unit for oral administration contains preferably from 1 to 200 mg of a compound of formula (1) or a pharmaceutically acceptable salt thereof calculated as the free base.

A dosage unit for parenteral administration preferably contains from 1 to 10 mg of a compound of formula (1) or a pharmaceutically acceptable salt thereof calculated as the free base.

The invention also provides a method of blocking histamine $H_1$-receptors which comprises administering to a subject an effective amount to block said receptors of a compound of formula (1) or a pharmaceutically acceptable salt thereof.

The compounds of formula (1) and their pharmaceutically acceptable salts will normally be administered to a subject in a pharmaceutical composition as described above, for the treatment of rhinitis, hayfever, bronchial asthma or allergic eczema. Typically the daily dosage regimen for an adult patient is between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

(i) 2-Bromopyridine (20 g), 1-3-diaminopropane (47 g) and pyridine (13 ml) were heated together under reflux for 2.5 hr. The mixture was stripped to remove excess diaminopropane and the residue taken up in water. The pH was adjusted to 14 and extracted with chloroform. The extracts were dried ($K_2CO_3$), stripped and the residue distilled at reduced pressure to give 2-(3-aminopropylamino)pyridine 13.3 g (70%) bp 90°–91° C., 0.02 mm Hg.

(ii) To a suspension of sodium hydride (0.82 g) in DMSO (20 ml) was added 2-(3-aminopropylamino)pyridine (4.7 g). The mixture was stirred and slowly heated under nitrogen to 85° C. After the evolution of hydrogen had ceased the mixture was cooled to room temperature and iodomethane (4.41 g) in DMSO (5 ml) added keeping the temperature below 35° C. After stirring for a further 30 minutes water (200 ml) was added and the resulting mixture extracted with chloroform. The extract was washed with water followed by 2N hydrochloric acid. The pH of the acid washings was raised to 14 (NaOH) and extracted again with chloroform. This final extract was dried ($K_2CO_3$) and stripped to an oil 3.84 g. Chromatography (silica gel, 10% ammoniacal methanol/dichloromethane) afforded 2-[N-(3-aminopropyl)-N-methylamino]pyridine 2.0 g (39%) as an oil.

(iii) 2-[N-(3-aminopropyl)-N-methylamino]pyridine (0.81 g) and 2-methylthio-5-phenylethylpyrimid-4-one (1.0 g) were heated together under reflux in pyridine (2.5 ml) for 26 hr. After stripping, the residue was crystallised twice from ethanol and finally from acetone to give 2-[3-(N-methyl-N-pyrid-2-ylamino)propylamino]-5-phenylethylpyrimid-4-one, 0.68 g (46%) mp 134°–136° C.

$C_{21}H_{25}N_5O$; Found C, 69.42; H, 7.10; N, 19.29; Requires C, 69.40; H, 6.83; N, 19.27%.

EXAMPLE 2

2-[N-(3-aminopropyl)-N-methylamino)pyridine (1.0 g) 2-nitroamino-5-benzylpyrimid-4-one (1.23 g) were heated together under reflux in pyridine (3 ml) for 18 hr. The mixture was stripped, the residue crystallised from ethyl acetate/water (trace) and chromatographed (silica gel, chloroform). Recrystallisation twice from ethyl acetate/water afforded 2-[3-(N-methyl-N-pyrid-2-ylamino)propylamino]-5-benzylpyrimid-4-one 0.3$H_2O$, 1.01 g (57%) mp 75°–85° C. (softens).

$C_{20}H_{23}N_5O$ 0.3 $H_2O$; Found C, 67.61; H, 6.68; N, 19.73; Requires C, 67.70; H, 6.70; N, 19.74%;

EXAMPLE 3

2-[N-(3-aminopropyl)-N-methylamino]pyridine (0.74 g) and 2-methylthio-5-(2-chlorobenzyl)pyrimid-4-one (1.0 g) were heated together under reflux in pyridine (2.5 ml) for 28 hr. After stripping, the residue was recrystallised twice from ethanol/water to give 2-[3-(N-methyl-N-pyrid-2-ylamino)propylamino]-5-(2-chlorobenzyl)pyrimid-4-one 0.5$H_2O$, 0.87 g (59%) mp 47°–49° C.

$C_{20}H_{22}ClN_5O$ 0.5 $H_2O$; Found C, 60.95; H, 5.61; N, 17.59; Cl, 9.31; Requires C, 61.20; H, 5.90; N, 17.84, Cl, 9.03%.

EXAMPLE 4

2-[N-(3-aminopropyl)-N-methylamino]pyridine (0.74 g) and 2-methylthio-5-(3-chlorobenzyl)pyrimid-4-one (0.8 g) were heated together under reflux in pyridine (2.5 ml) for 26 hr. After stripping, the residue was recrystallised three times from ethanol/water to give 2-[3-(N-methyl-N-pyrid-2-ylamino) propylamino]-5-(3-chlorobenzyl)pyrimid-4-one 1H$_2$O, 0.7 g (58%) mp 105°-7° C.

$C_{20}H_{22}ClN_5O$ H$_2$O, Found C, 59.70; H, 6.04; N, 17.71; Cl, 8.54. Requires C, 59.77; H, 6.02; N, 17.43; Cl, 8.82%.

EXAMPLE 5

2-[N-(3-aminopropyl)-N-methylamino]pyridine (0.66 g) and 2-methylthio-5-(3,4-dichlorobenzyl)pyrimid-4-one (1.0 g) were heated together under reflux in pyridine (2.5 ml) for 24 hr. After stripping, the residue was recrystallised three times from ethanol/water to give 2-[3-(N-methyl-N-pyrid-2-ylamino)propylamino]-5-(3,4-dichlorobenzyl)pyrimid-4-one 0.25H$_2$O, 1.0 g (70%) mp 104°-6° C.

$C_{20}H_{21}Cl_2N_5O$ 0.25 H$_2$O; Found C, 57.01; H, 5.24; N, 16.63; Cl, 16.49; Requires C, 56.81; H, 5.13; N, 16.56; Cl, 16.77%.

EXAMPLE 6

2-[N-(3-aminopropyl)-N-methylamino]pyridine (1.98 g) and 2-methylthio-5-(4-hydroxybenzyl)pyrimid-4-one (2.48 g) were heated together under reflux in pyridine (5 ml) for 24 hr. After stripping, the residue was triturated with water (pH adjusted to 7.0 with 2N hydrochloric acid). Recrystallisation from ethanol/water and again from methanol gave 2-[3-(N-methyl-N-pyrid-2-ylamino)propyl-amino]-5-(4-hydroxybenzyl) pyrimid-4-one, 2.4 g (66%) mp 109°-11° C. (analytical sample from methanol).

$C_{20}H_{23}N_5O_2$ 0.35 H$_2$O; Found C, 64.62; H, 6.34; N, 18.91; Requires C, 64.62; H, 6.43; N, 18.84%.

EXAMPLE 7

2-[3-(N-methyl-N-pyrid-2-ylamino)propylamino]-5(4-hydroxybenzyl) pyrimid-4-one (1.5 g) was dissolved in nitric acid (2N, 30 ml). After standing for 30 min the pH was raised to ca. 6.5 with sodium hydroxide and the precipitate chromatographed (silica gel, graded elution chloroform/methanol 1:0 to 10:1). Recrystalisation twice from methanol/water gave 2-[3-(N-methyl-N-pyrid-2-ylamino)-propylaminol]-5-(4-hydroxy-3-nitrobenzyl) pyrimid-4-one 1.2H$_2$O, 0.81 g (46%) mp 90°-93° C.

$C_{20}H_{22}N_6O_4$ 1.2 H$_2$O; Found C, 55.39; H, 5.4; N, 19.41; Requires C, 55.60; H, 5.69; N, 19.45%.

EXAMPLE 8

2-[N-(3-aminopropyl)-N-methylamino]pyridine (1.0 g) and 2-methylthio-5-(4-bromobenzyl)pyrimid-4-one (1.56 g) were heated together under reflux in pyridine (3 ml) for 18 hr. The mixture was stripped and the residue recrystallised three times from ethanol to give 2-[3-(N-methyl-N-pyrid-2-ylamino) propylamino]-5-(4-bromobenzyl)pyrimid-4-one, 1.45 g (67%) mp 178°-9° C.

$C_{20}H_{22}BrN_5O$; Found C, 55.96; H, 5.17; N, 16.6; Br, 18.79; Requires C, 56.08; H, 5.18; N, 16.35; Br, 18.66%;

EXAMPLE 9

2-[N-(3-aminopropyl)-N-methylamino]pyridine (0.81 g) and 2-methylthio-5-(4-methylbenzyl)pyrimid-4-one (1.0 g) were heated together under reflux in pyridine (2.5 ml) for 26 hr. The mixture was stripped and the residue recrystallised twice from ethanol/water to give 2-[3-(N-methyl-N-pyrid-2-ylamino) propylamino]-5-(4-methylbenzyl)-pryrimid-4-one 0.8H$_2$O, 0.8 g (52%) mp indeterminate.

$C_{21}H_{25}N_5O$ 0.8 H$_2$O; Found C, 66.88; H, 7.16; N, 18.55; Requires C, 66.62; H, 7.10; N, 18.50%.

EXAMPLE 10

2-[N-(3-aminopropyl)-N-methylamino]pyridine (1.0 g) and 2-methylthio-5-(4-chlorobenzyl)pyrimid-4-one (1.33 g) were heated together under reflux in pyridine (3 ml) for 20 hr. The mixture was stripped and the residue recrystallised twice from ethanol to give 2-[3-(N-methyl-N-pyrid-2-ylamino) propylamino]-5-(4-chlorobenzyl)pyrimid-4-one 0.5H$_2$O. 1.16 g (59%) mp ca. 65° C. (softens).

$C_{20}H_{22}ClN_5O$ 0.5 H$_2$O; Found C, 61.33; H, 6.08; N, 17.56; Cl, 8.77; Requires C, 61.14; H, 5.90; N, 17.83; Cl, 9.02%.

EXAMPLE 11

2-[N-(3-aminopropyl)-N-methylamino]pyridine (1.0 g) and 2-methylthio-5-(4-fluorobenzyl)pyrimid-4-one (1.25 g) were heated together under reflux in pyridine (3 ml) for 24 hr. The mixture was stripped and the residue recrystallised twice from ethanol/water to give 2-[3-(N-methyl-N-pyrid-2-ylamino) propylamino]-5-(4-fluorobenzyl)-pyrimid-4-one 0.5H$_2$O, 1.2 g (64%) mp ca. 70° C. (softens).

$C_{20}H_{22}FN_5O$ 0.5 H$_2$O; Found C, 63.85; H, 5.92; N, 18.59; Requires C, 63.81; H, 6.16; N, 18.61%.

EXAMPLE 12

2-[N-(3-aminopyropyl)-N-methylamino]pyridine (1.0 g) and 2-methylthio-5-(4-methoxybenzyl)pyrimid-4-one (1.31 g) were heated together under reflux in pyridine (3 ml) for 24 hr. The mixture was stripped and the residue recrystallised twice from ethanol/water to give 2-[3-(N-methyl-N-pyrid-2-ylamino) propylamino]-5-(4-methoxybenzyl) pyrimid-4-one 0.25H$_2$O, 1.1 g (57%) mp softens ca. 60° C. melts 148°-9° C.

$C_{21}H_{25}N_5O_2$ 0.25 H$_2$O; Found C, 65.54; H, 6.48; N, 18.13; Requires C, 65.69; H, 6.69; N, 18.24%.

EXAMPLE 13

2-[N-(3-aminopropyl)-N-methylamino]pyridine (1.7 g) and 2-nitroamino-5-(6-methylpyrid-3-ylmethyl)-pyrimid-4-one (1.8 g) were heated together in pyridine (10 ml) for 22 hr. The mixture was stripped and the residue triturated with wet ether. Recrystallisation from isopropanol/water and ethanol/water gave 2-[3-(N-methyl-N-pyrid-2-ylamino)propyl-amino]-5-(6-methyl-pyrid-3ylmethyl) pyrimid-4-one 0.25H$_2$O, 1.36 g (53%) mp 86°-92° C.

$C_{20}H_{24}N_6O$ 0.25 H$_2$O; Found C, 65.06; H, 6.84; N, 22.71. Requires C, 65.11; H, 6.69; N, 22.78%.

EXAMPLE 14

(i) To a suspension of sodium hydride (0.78 g) in DMSO (20 ml) was added 2-(N-phenylamino)pyridine (5.0 g) in DMSO (15 ml). The mixture was stirred and slowly heated under nitrogen to 85° C. After the evolution of hydrogen had ceased the mixture was cooled to room temperature and N-(3-bromopropyl)phthalimide (7.88 g) in DMSO (15 ml) added dropwise. After standing overnight the mixture was poured into water and ether extracts made with the pH adjusted between 2 to 4. The extracts were dried (MgSO$_4$), stripped and the residue crystallised from ethanol to give N-[3-(N-phenyl-N-pyrid-2-ylamino)propyl]phthalimide, 3.69 g (35%) mp 103°–5° C. (ii) N-[3-(N-phenyl-N-pyrid-2-ylamino)propyl]phthalimide (3.1 g) and conc. hydrochloric acid (30 ml) were heated under reflux for 21 hr. Phthalic acid was filtered off on cooling and the filtrate stripped. The residue was taken back up in water and the solution extracted at pH 1 with chloroform. The pH was raised to 13 (NaOH) and the solution extracted again with ether. The ether extracts were dried (K$_2$CO$_3$) and stripped to give 2-[N-(3-aminopropyl)-N-phenylamino]pyridine, 1.84 g as an oil. (iii) 2-[N-(3-aminopropyl)-N-phenylamino]pyridine (0.9 g) and 2-nitroamino-5-(6-methylpyrid-3-ylmethyl)pyrimid-4-one (0.86 g) were heated together under reflux in pyridine (2.5 ml) for 24 hr. The mixture was stripped and the residue recrystallised from ethanol to give 2-[3-(N-phenyl-N-pyrid-2-ylamino) propylamino]-5-(6-methylpyrid-3-ylmethyl) pyrimid-4-one, 1.03 g (73%) mp 216°–18° C.

C$_{25}$H$_{26}$N$_6$O; Found C, 70.42; H, 6.31; N, 19.85; Requires C, 70.40; H, 6.14; N, 19.71%.

EXAMPLE 15

(i) Sodium hydride (1.14 g) was dissolved in DMSO (20 ml) at 70°–75° C. The solution was cooled and 2-(3-aminopropylamino)pyridine (6.57 g) in DMSO (20 ml) added at room temperature. n-Propyl iodide (8.13 g) in DMSO (10 ml) was added dropwise maintaining the temperature at 20–25° C. After standing overnight, water (250 ml) was added and the mixture extracted with ether. The ether extracts were washed with 2N hydrochloric acid and the aqueous layers basified to pH 10.5. After extracting with ether and chloroform the pH was raised to 14 and again extracted with ether. After drying (K$_2$CO$_3$), the final ether extract, on stripping, afforded 2-[N-(3-aminopropyl)-N-propylamino]pyridine (3.4 g) as an oil which was used without further purification. (ii) 2-[N-(3-aminopropyl)-N-propylamino]-pyridine (1.74 g) and 2-methylthio-5-(4-chlorobenzyl)-pyrimid-4-one (1.6 g) were fused together on an oil bath at 160° C. for 2 hr. On cooling the residue was crystallised three times from ethanol to give 2-[3(N-propyl-N-pyrid-2-ylamino)propylamino]-5-(4-chlorobenzyl)-pyrimid-4-one 1.1H$_2$O, 0.8 g (31%) mp 120°–28° C. (softens).

C$_{22}$H$_{26}$ClN$_5$O 1.1 H$_2$O; Found C, 61.09; H, 6.68; N, 16.21; Cl, 8.27. Requires C, 61.20; H, 6.58; N, 16.22; Cl, 8.21%.

EXAMPLE 16

2-[N-(3-aminopropyl)-N-methylamino]pyridine (1.33 g) and 2-nitroamino-5-(6-methylpyrid-3-ylmethyl)-pyrimid-4-one (1.5 g) were heated together under reflux in pyridine (10 ml) for 24 hr. The mixture was stripped and the residue triturated with wet ether. Recrystallisation three times from ethanol/water gave 2-[3-(N-propyl-N-pyrid-2-ylamino) propylamino)-5-(6-methylpyrid-3-ylmethyl)pyrimid-4-one 0.9H$_2$O, 1.45 g (62%) mp 83°–90° C. (softens).

C$_{22}$H$_{28}$N$_6$O 0.9 H$_2$O; Found C, 64.39; H, 7.35; N, 20.78; Requires C, 64.65; H, 7.35; N, 20.56%.

EXAMPLE 17

(i) A mixture of sodium hydride (0.7 g) and 2-(3-aminopropylamino)pyridine (4.02 g) in DMSO (25 ml) was heated slowly to 75° C. under nitrogen. After the evolution of hydrogen had ceased the solution was cooled to room temperature and benzyl bromide (3.17 ml) added dropwise below 35° C. After a further 30 minutes water was added and the mixture extracted with chloroform. The chloroform extracts were washed with 2N hydrochloric acid, the pH of the aqueous layers ajusted to 4.5 and re-extracted with chloroform. The pH was further raised to 14 and again extracted with chloroform. After drying (K$_2$CO$_3$), the final chloroform extract, on stripping, afforded 2-[N-(3-aminopropyl)-N-benzylamino]pyridine as an oil (3.91 g) which was used without further purification. (ii) 2-[N-(3-aminopropyl)-N-benzylamino]pyridine (1.64 g) and 2-nitroamino-5-(6-methylpyrid-3-ylmethyl)pyrimid-4-one (1.48 g) were heated together under reflux in pyridine (15 ml) for 20 hr. After stripping the residue was treated with wet ether and the resulting solid recrystallised from ethanol/water to give 2-[3-(N-benzyl-N-pyrid-2-ylamino)propylamino]-5-(6-methylpyrid-3-ylmethyl)-pyrimid-4-one 0.75H$_2$O, 1.46 g (56%) mp 90°–96° C.

C$_{26}$H$_{28}$N$_6$O 0.75 H$_2$O; Found C, 68.90; H, 6.61; N, 18.27; Requires C, 68.77; H, 6.55; N, 18.51%.

EXAMPLE 18

2-[N-(3-aminopropyl)-N-benzylamino]pyridine (1.45 g) and 2-methylthio-5-(4-chlorobenzyl)pyrimid-4-one (1.33 g) were fused together on an oil bath at 160° C. for 3 hr. On cooling, the residue was crystallised from ethanol and then chromatographed (silica gel, chloroform). Fractions containing the required product were stripped and the residue recrystallised from ethanol to give 2-[3-(N-benzyl-N-pyrid-2-ylamino) propylamino]-5-(4-chlorobenzyl)pyrimid-4-one 0.25H$_2$O, 0.9 g (39%) mp 80°–86° C.

C$_{26}$H$_{26}$ClN$_5$O 0.25 H$_2$O; Found C, 67.21; H, 5.66; N, 14.99; Cl, 7.47; Requires C, 67.23; H, 5.75; N, 15.08; Cl, 7.63%.

EXAMPLE 19

(i) Sodium hydride (1.32 g) was dissolved in DMSO (25 ml) at 70°–75° C. under nitrogen. The solution was cooled and 2-(3-aminopropylamino)pyridine (7.56 g) in DMSO (20 ml) added at room temperature. 3-Chlorobenzyl chloride (8.86 g) in DMSO (15 ml) was added dropwise maintaining the temperature at 20°–25° C. After a further 1 hour, water was added (200 ml) and the mixture extracted with ether. The ether extracts were washed with 2N hydrochloric acid and the aqueous layer adjusted to pH 3.5. After extracting with chloroform the pH was raised to 14 and extracted with ether. After drying (K$_2$CO$_3$), the final ether extracts were stripped to give 2-[N-(3-aminopropyl)-N-(3-chlorobenzyl) amino]pyridine (8.34 g) as an oil which was used without further purification. (ii) 2-[N-(3-aminopropyl)-N-(3-chlorobenzyl)amino]pyridine (1.65 g) and 2-nitroamino-5-(6-methylpyrid-3-ylmethyl)-pyrimid-4-one (1.3 g) were heated together under reflux in pyridine (15 ml) for 20 hr. On cooling, the mixture was stripped, the residue triturated with wet ether and recrystallised twice from ethanol/water to give 2-[3-[N-(3-chlorobenzyl)-N-pyrid-2-ylamino]propylamino]-5-

(6-methylpyrid-3-ylmethyl) pyrimid-4-one 0.6H$_2$O, 1.29 g (53%) mp 100°-104° C.

C$_{26}$H$_{27}$ClN$_6$O 0.6 H$_2$O. Found C, 64.31; H, 5.79; N, 17.51; Cl, 7.19; Requires C, 64.28; H, 5.85; N, 17.30; Cl, 7.30%.

EXAMPLE 20

(i) A mixture of sodium hydride (1.12 g) and 2-(3-amino-propylamino) pyridine (7.05 g) in DMSO (30 ml) was heated slowly to 85° C. under nitrogen. After the evolution of hydrogen had ceased the solution was cooled to room temperature and 4-chlorobenzyl chloride (5.95 ml) in DMSO (10 ml) added dropwise keeping the temperature below 30° C. After standing for 72 hr, water (300 ml) was added and the mixture extracted with ether. The extract was washed with water and 2N hydrochloric acid. The pH of the acid washing was raised to 6 and extracted with ether. The pH was raised further to 14 and extracted again with ether. After drying (MgSO$_4$) and stripping, the final ether extract gave 2-[N-(3-aminopropyl)-N-(4-chlorobenzyl)amino]pyridine (7.43 g) as an oil, bp 160° C. 0.04 mm Hg. (ii) 2-[N-(3-aminopropyl)-N-(4-chlorobenzyl)amino]pyridine (1.25 g) and 2-nitroamino-5-(6-methylpyrid-3-ylmethyl)pyrimid-4-one (1.08 g) were heated together under reflux in pyridine (10ml) for 20 hr. On cooling, the mixture was stripped, the residue triturated with wet ether and recrystallised from isopropanol/water to give 2-[3-[N-(4-chlorobenzyl)-N-pyrid-2-ylamino]propylamino]-5-(6-methyl-pyrid-3-ylmethyl) pyrimid-4-one 1H$_2$O, 1.68 g (83%) mp 88°-92° C.

C$_{26}$H$_{27}$ClN$_6$O H$_2$O; Found C, 63.20; H, 5.84; N, 16.95; Cl, 6.95; Requires C, 63.34; H, 5.93; N, 17.05; Cl, 7.19%.

EXAMPLE 21

(i) A mixture of sodium hydride (0.95 g) and 2-(3-aminopropylamino) pyridine (5.4 g) in DMSO (25 ml) was heated slowly to 85° C. under nitrogen. After the evolution of hydrogen had ceased the solution was cooled to room temperature and 4-methoxybenzyl chloride (5.59 g) in DMSO (5 ml) added dropwise keeping the temperature below 30° C. After a further 1 hr, water (300 ml) was added and the mixture extracted with ether. The extract was washed with 2N hydrochloric acid. The pH of the acid washings was adjusted to 4-5. After extracting with chloroform the pH was raised to 14 and extracted with ether. The ether extract was washed with water, dried (K$_2$CO$_3$) and stripped to give 2-[N-(3-aminopropyl)-N-(4-methoxybenzyl)-amino]-pyridine (7.19 g) as an oil which was used without further purification. (ii) 2-[N-(3-aminopropyl)-N-(4-methoxybenzyl)amino]pyridine (1.0 g) and 2-nitroamino-5-(6-methylpyrid-3-ylmethyl)pyrimid-4-one (0.8 g) were heated together under reflux in pyridine (10 ml) for 20 hr. On cooling, the mixture was stripped, the residue triturated with ether and recrystallised twice from ethanol/water to give 2-[3-[N-(4-methoxybenzyl)-N-pyrid-2-ylamino]propylamino]-5-(6-methylpyrid-3-ylmethyl)pyrimid-4-one 1H$_2$O, 0.72 g (48%), mp 90°-98° C. (softens).

C$_{27}$H$_{30}$N$_6$O$_2$ H$_2$O; Found C, 66.29; H, 6.5; N, 17.09; Requires C, 66.37; H, 6.6; N, 17.20%.

EXAMPLE 22

(i) 2-Bromopyridine (15.8 g), ethylene diamine (30 g) and pyridine (10 ml) were heated together under reflux for 3 hr. The mixture was stripped to remove the excess of ethylene diamine and the residue taken up in water. The pH was adjusted to 14 and extracted with chloroform. The extracts were dried (K$_2$CO$_3$), stripped and the residue distilled at reduced pressure to give 2-(2-aminoethylamino) pyridine, 8.24 g (60%) bp 80° C., 0.01 mm Hg. (ii) A mixture of sodium hydride (0.53 g) and 2-(aminoethylamino)pyridine (2.74 g) in DMSO (30 ml) was heated slowly to 85° C. under nitrogen. After the evolution of hydrogen had ceased the solution was cooled to room temperature and benzyl bromide (2.37 ml) added dropwise keeping the temperature below 30° C. After a further 1 hr, water (200 ml) was added, the mixture extracted with ether and the extract washed with 2N hydrochloric acid. The pH of the aqueous layer was adjusted to 4.5 and extracted with chloroform. The pH was further raised to 14 and extracted with ether. After drying (K$_2$CO$_3$) and stripping, the final ether extract gave 2-[N-(2-aminoethyl)-N-benzylamino]pyridine (2.58 g) as an oil which was used without further purification.

(iii) 2-[N-(2-aminoethyl)-N-benzylamino]pyridine (0.95 g) and 2-nitroamino-5-(6-methylpyrid-3-ylmethyl)pyrimid-4-one (0.91 g) were heated together under reflux in pyridine (10 ml) for 20 hr. After stripping, the residue was triturated with ether and recrystallised from methanol to give 2-[2-(N-benzyl-N-pyrid-2-ylamino)ethylamino]-5-(6methylpyrid-3-ylmethyl) pyrimid-4-one, 1.02 g (68%) mp 178°-82° C.

C$_{25}$H$_{26}$N$_6$O; Found C, 70.10; H, 5.91; N, 19.51; Requires C, 70.40; H, 6.14; N, 19.71%.

EXAMPLE 23

(i) Sodium hydride (1.32 g) was disolved in DMSO (25 ml) at 70°-75° C. under nitrogen. The solution was cooled and 2-(3-aminopropylamino)pyridine (7.5 g) added at room temperature. 2-Chlorobenzyl chloride (8.86 g) in DMSO (15 ml) was added dropwise maintaining the temperature at 20°-25° C. After standing overnight water (200 ml) was added and the mixture extracted with ether. The ether extracts were washed with 2N hydrochloric acid and after partitioning into ether and chloroform at pH 3.5 and 14, an oil was obtained which was further purified by HPLC (silica gel, dichloromethane then 2% ammoniacal methanol/dichloromethane) to give 2-[N-(3-aminopropyl)-N-(2-chlorobenzyl) amino]pyridine (3.44 g) as an oil.

(ii) 2-[N-(3-aminopropyl)-N-(2-chlorobenzyl)amino]pyridine (1 g) and 2-nitroamino-5-(6-methylpyrid-3-ylmethyl)pyrimid-4-one (0.78 g) were heated together under reflux in pyridine (10 ml) for 20 hr. After stripping, the residue was triturated with ether and recrystallised twice from ethanol/water to give 2-[3-[N-(2-chlorobenzyl)-N-pyrid-2-ylamino]propylamino]-5-(6-methylpyrid-3-ylmethyl)-pyrimid-4-one 0.4H$_2$O, 0.34 g (20%) mp softens 94°-102° C. melts 120°-26° C.

C$_{26}$H$_{28}$ClN$_6$O 0.4H$_2$O; Found C, 64.66; H, 5.79; N, 17.27; Requires C, 64.62; H, 6.01; N, 17.39%.

EXAMPLE 24

2-[N-(3-aminopropyl)-N-propylamino]pyridine (0.88 g) and 2-methylthio-5-(4-methoxybenzyl)pyrimid-4-one (1.0 g) were fused together on an oil bath at 160° C. for 2.5 hr. On cooling the residue was crystallised from ethanol/water and again from acetone/water to give 2-[3-(N-propyl-N-pyrid-2-ylamino) propylamino]-5-(4-methoxybenzyl)pyrimid-4-one 1H$_2$O, 1.27 g (79%) mp indeterminate.

$C_{23}H_{29}N_5O_2 \cdot H_2O$; Found C, 65.23; H, 7.23; N, 16.66; Requires C, 64.92; H, 7.34; N, 16.46%.

EXAMPLE 25

2-[N-(3-aminopropyl)-N-propylamino]pyridine (1.0 g) and 2-methylthio-5-(3,4-methylenedioxybenzyl)-pyrimid-4-one (1.14 g) were heated together under reflux for 16 hr. After stripping, the residue was crystallised from ethanol/water to give 2-[3-(N-propyl-N-pyrid-2-ylamino)propylamino]-5-(3,4-methylenedioxybenzyl) pyrimid-4-one 1H$_2$O, 1.47 g (81%) mp 86°–92° C.

$C_{23}H_{27}N_5O_3 \cdot 1H_2O$; Found C, 62.74; H, 6.64; N, 15.99; Requires C, 62.85; H, 6.65; N, 15.94%.

EXAMPLE 26

2-[N-(3-aminopropyl)-N-propylamino]pyridine (1.16 g) and 2-methylthio-5-(4-fluorobenzyl)pyrimid-4-one (1.25 g) were fused together on an oil bath at 160° C. for 5 hr. On cooling the residue was crystallised twice from ethanol and finally from ethanol/water to give 2-[3-(N-propyl-N-pyrid-2-ylamino) propylamino]-5-(4-fluorobenzyl)pyrimid-4-one 1.2H$_2$O, 0.75 g (36%) mp 107°–9° C.

$C_{22}H_{26}FN_5O \cdot 1.2\ H_2O$; Found C, 63.3; H, 6.91; N, 16.79; Requires C, 63.35; H, 6.86; N, 16.79%.

EXAMPLE 27

(i) A mixture of sodium hydride (0.96 g) and 2-(2-amino-ethylamino) pyridine (5.0 g) in DMSO (50 ml) were heated slowly to 85° C. under nitrogen. After the evolution of hydrogen had ceased the solution was cooled to room temperature and methyl iodide (2.5 ml) in DMSO (10 ml) added dropwise below 25° C. After a further 1.5 hr the mixture was poured into water and extracted with ether and chloroform. The volume of the extracts was reduced and washed with 2N hydrochloric acid. Partitioning between water, ether and dichloromethane at pH 1 and 13 gave, on stripping the final basic extract, 2-[N-(2-aminoethyl)-N-methylamino]pyridine (4.43 g) as an oil which was used without further purification. (ii) 2-[N-(2-aminoethyl)-N-methylamino]pyridine (0.68 g) and 2-methylthio-5-(4-chlorobenzyl)pyrimid-4-one (1.0 g) were heated together under reflux in pyridine (2.5 ml) for 30 hr. After stripping the residue was crystallised from ethanol/water to give 2-[2-(N-methyl-N-pyrid-2-ylamino)ethylamino]-5-(4-chlorobenzyl)pyrimid-4-one 0.1 1H$_2$O, 0.76 g (54%) mp 172°–74° C.

$C_{19}H_{20}ClN_5O \cdot 0.1\ H_2O$; Found C, 61.31; H, 5.24; N, 18.63; Cl, 9.31; Requires C, 61.40; H, 5.48; N, 18.84; Cl, 9.54%.

EXAMPLE 28

(i) 2-Bromopyridine (10 g), 1,4-diaminobutane (35 ml) and pyridine (7 ml) were heated together under reflux for 4 hr. The mixture was stripped to remove the excess of diaminobutane and the residue taken up in water. The solution was extracted with chloroform at pH 7 and 13. After drying (K$_2$CO$_3$) the latter extract was stripped and the residue distilled at reduced pressure to give 2-(4-amino-butylamino) pyridine 7.0 g (67%) bp 136°–38° C., 2 mm Hg. (ii) A mixture of sodium hydride (0.78 g) and 2-(4-aminobutylamino) pyridine (4.9 g) in DMSO (45 ml) was heated slowly to 85° C. under nitrogen. After the evolution of hydrogen had ceased the solution was cooled to room temperature and methyl iodide (2.1 ml) in DMSO (10 ml) added dropwise below 25° C. After a further 1.5 hr the mixture was poured into water (150 ml) and extracted with dichloromethane. The volume of the extract was reduced and washed with 2N hydrochloric acid. Partitioning between water, ether and dichloromethane at pH 1 and 13 gave, on stripping the final basic extract, 2-[N-(4-aminobutyl)-N-methylamino]pyridine (3.22 g) as an oil which was used without further purification. (iii) 2-[N-(4-aminobutyl)-N-methylamino]pyridine (0.81 g) and 2-methylthio-5-(4-chlorobenzyl)pyrimid-4-one (1.0 g) were heated together under reflux in pyridine (2.5 ml) for 23 hr. After stripping, the residue was crystallised twice from ethanol/water to give 2-[4-(N-methyl-N-pyrid-2-ylamino)butylamino]-5-(4-chlorobenzyl)pyrimid-4-one 1.5H$_2$O, 0.98 g (62%) mp softens 72–75 melts 133°–35° C.

$C_{21}H_{24}ClN_5O \cdot 1.5\ H_2O$; Found C, 59.59; H, 6.29; N, 16.33; Cl, 8.33; Requires C, 59.36; H, 6.3; N, 16.48; Cl, 8.34%.

EXAMPLE 29

(i) Sodium hydride (1.6 g) was disolved in DMSO (35 ml) at 70°–75° C. under nitrogen. The solution was cooled and 2-(4-aminobutylamino)pyridine (10 g) in DMSO (10 ml) added at room temperature. Benzyl bromide (10.35 g) in DMSO (10 ml) was added dropwise maintaining the temperature at 25°–30° C. After a further 2 hr water (200 ml) was added and the mixture extracted with chloroform. The chloroform extract was washed with 2N hydrochloric acid and the aqueous layer basified to pH 4. After extracting with chloroform the pH was raised to 14 and again extracted with chloroform. After stripping the latter extract the residue was taken up in ether and the solution washed with water. The ether layer was dried (K$_2$CO$_3$) and stripped to give 2-[N-(4-aminobutyl)-N-benzylamino]pyridine (5.61 g) as an oil which was used without further purification. (ii) 2-[N-(4-aminobutyl)-N-benzylamino]pyridine (1 g) and 2-nitroamino-5-(6-methylpyrid-3-ylmethyl)pyrimid-4-one (0.82 g) were heated together under reflux in pyridine (5 ml) for 22 hr. After cooling the mixture was stripped, the residue triturated with ether and crystallised from ethanol/ether to give 2-[4-(N-benzyl-N-pyrid-2-ylamino)butylamino]-5-(6-methylpyrid-3-ylmethyl)pyrimid-4-one 0.4H$_2$O, 1.15 g (80%) mp softens 98°–100° C. melts 120°–22° C. (from ethanol/water).

$C_{27}H_{30}N_6O \cdot 0.4\ H_2O$; Found C, 70.21; H, 6.87; N, 18.35; Requires C, 70.22; H, 6.72; N, 18.20%.

EXAMPLE 30

(i) Sodium hydride (1.1 g) was disolved in DMSO (20 ml) at 70°–75° C. under nitrogen. The solution was cooled and 2-(4-aminobutylamino)pyridine (6.9 g) in DMSO (20 ml) added at room temperature. n-Propyl iodide (7.81 g) in DMSO (10 ml) was added dropwise maintaining the temperature at 25°–35° C. After a further 15 min water (200 ml) was added and the mixture extracted with ether. The ether extract was washed with 2N hydrochloric acid and the aqueous layer basified to pH 6. After extracting with chloroform, the pH of the aqueous layer was raised to 14 and extracted with ether. The ether extracts were washed with 0.1N sodium hydroxide, dried (K$_2$CO$_3$) and stripped to give 2-[N-(4-aminobutyl)-N-propylamino]pyridine (5.79 g) as an oil which was used without further purification. (ii) 2-[N-(4-aminobutyl)-N-propylamino]pyridine (1.24 g) and 2-methylthio-5-(3,4-methylenedioxybenzyl)- pyrimid-4-one (1.38 g) were fused together in an oil bath at 160° C. for 2.5 hr. On cooling the residue was crystallised twice from ethanol/water and finally from acetone/water to give 2-[4-(N-propyl-N-pyrid-2-ylamino)butylamino]-5-(3,4-methylenedioxybenzyl)-pyrimid-4-one 1.95H$_2$O, 1.11 g (47%) mp indeterminate.

C$_{24}$H$_{29}$N$_5$O$_3$ 1.95 H$_2$O; Found C, 61.49; H, 6.77; N, 15.06; Requires C, 61.26; H, 7.05; N, 14.88%.

EXAMPLE 31

2-[N-(4-aminobutyl)-N-propylamino]pyridine (1.24 g) and 2-methylthio-5-(4-chlorobenzyl)pyrimid-4-one (1.33 g) were fused together on an oil bath at 160° C. for 3 hr. On cooling the residue was crystallised from ethanol/water (drop 2N HCl added to pH6) to give a white solid (2.05 g). Recrystallisation from ethanol/water gave 2-[4-(N-propyl-N-pyrid-2-ylamino)-butylamino]-5-(4-chlorobenzyl)pyrimid-4-one 0.43H$_2$O, 0.88 g (40%) mp indeterminate.

C$_{23}$H$_{28}$ClN$_5$O 2 H$_2$O; Found C, 59.99; H, 6.68; N, 15.39; Cl, 7.43; Requires C, 59.79; H, 6.98; N, 15.16; Cl, 7.67%.

EXAMPLE 32

2-[N-(4-aminobutyl)-N-propylamino]pyridine (1.24 g) and 2-methylthio-5-(4-fluorobenzyl)pyrimid-4-one (1.25 g) were fused together on an oil bath at 160° C. for 2.5 hr. On cooling the residue was crystallised twice from ethanol/water to give 2-[4-(N-propyl-N-pyrid-2-ylamino)butylamino]5-(4-fluorobenzyl)pyrimid-4-one 1.25H$_2$O, 0.56 g (26.%) mp indeterminate.

C$_{23}$H$_{28}$FN$_5$O 1.25 H$_2$O; Found C, 63.97. H, 7.01; N, 16.21; Requires C, 63.94; H, 7.12; N, 16.21%.

EXAMPLE 33

2-[N-(4-aminobutyl)-N-propylamino]pyridine (1.0 g) and 2-methylthio-5-(4-methoxybenzyl)pyrimid-4-one (0.95 g) were fused together on an oil bath at 160° C. for 2.5 hr. On cooling the residue was crystallised from ethanol/water to give a white solid which on recrystallisation from acetone water gave 2-[4-(N-propyl-N-pyrid-2-ylamino)butylamino]-5-(4-methoxybenzyl)-pyrimid-4-one 0.25H$_2$O, 1.02 g (63%) mp 122°-24° C.

C$_{24}$H$_{31}$N$_5$O$_2$ 0.25 H$_2$O; Found C, 67.90; H, 7.39; N, 16.60; Requires C, 67.66; H, 7.45; N, 16.44%.

EXAMPLE 34

(i) A mixture of 1,3-diaminopropane (17.6 ml), 2,5-dibromopyridine (10 g) and pyridine (5 ml) was heated under reflux for 4 hr. After stripping off the excess of 1,3-diaminopropane, the residue was taken up in water, the pH adjusted to 7 (conc. hydrochloric acid) and the solution extracted with chloroform. The pH was raised to 14 and extracted with chloroform. After drying (K$_2$CO$_3$), the final extract was evaporated to give 2-(3-aminopropylamino)-5-bromopyridine (9.1 g) as an oil which was used without further purification. (ii) To a suspension of sodium hydride (0.3 g) in DMSO (20 ml) was added 2-(3-aminopropylamino)-5-bromopyridine (2.88 g). The mixture was stirred and heated slowly to 85° C. After the evolution of hydrogen had ceased the mixture was cooled to room temperature and methyl iodide (1.77 g) in DMSO (5 ml) added dropwise maintaining the temperature below 30° C. After a further 15 min water (150 ml) was added and the mixture extracted with chloroform. The chloroform extract was washed with water and extracted with 1N hydrochloric acid. The acid extract was washed with chloroform, the pH adjusted to 13 (2N NaOH) and extracted again with chloroform. The final extract was stripped and the residue chromatographed (silica gel, 5% ammoniacal methanol/dichloromethane) to give 2-[N-(3-aminopropyl)-N-methylamino]-5-bromopyridine (1.44 g) as an oil which was used without further purification. (iii) 2-[N-(3-aminopropyl)-N-methylamino]-5-bromopyridine (1.4 g) and 2-nitroamino-5-(6-methylpyrid-3-ylmethyl)-pyrimid-4-one (1.25 g) were heated together under reflux in pyridine (10 ml) for 20 hr. After stripping, the residue was triturated with wet ether and recrystallised from isopropanol/water to give 2-[3-[N-methyl-N-(5-bromopyrimid-2-yl)amino]propylamino]-5-(6-methyl-pyrid-3-yl-methyl)pyrimid-4-one, 1.5 g (71%) mp 137°-40° C.

C$_{20}$H$_{23}$BrN$_6$O; Found C, 53.84; H, 5.17; N, 18.96; Br, 18.20; Requires C, 54.18; H, 5.23; N, 18.96; Br, 18.02%.

EXAMPLE 35

(i) To a suspension of sodium hydride (0.83 g) in DMSO (25 ml) was added 2-(3-aminopropylamino)-5-bromopyridine (4.6 g). The mixture was stirred and heated slowly, to 85° C. After the evolution of hydrogen had ceased the mixture was cooled to room temperature and benzyl bromide (3.42 g) in DMSO (5 ml) added dropwise maintaining the temperature below 30° C. After standing overnight, water was added and the mixture extracted with ether. The ether extract was washed with 2N hydrochloric acid. The pH of the acid extract was raised to 2.5 (NaOH) and extracted with chloroform. The pH was raised further to 14 and again extracted with chloroform. After drying (K$_2$CO$_3$), the final extract was stripped to give 2-[N-(3-aminopropyl)-N-benzylamino]-5-bromopyridine (4.6 g) as an oil which was used without further purification. (ii) 2-[N-(3-aminopropyl)-N-benzylamino]-5-bromopyridine (1.97 g) and 2-nitroamino-5-(6-methylpyrid-3-ylmethyl)pyrimid-4-one (1.34 g) were heated together under reflux in pyridine (15 ml) for 20 hr. After stripping, the residue was triturated with ether, recrystallised from methanol and chromatographed (silica gel, 1-2% methanol/chloroform) to give 2-[3-[N-benzyl-N-(5-bromopyrid-2-yl)-amino]propylamino]-5-(6-methylpyrid-3-ylmethyl)pyrimid-4-one, 0.2H$_2$O, 1.01 g (38%) mp 150°-55° C. (from ethanol).

C$_{26}$H$_{27}$BrN$_6$O.0.2H$_2$O; Found C, 59.87; H, 5.14; N, 16.06; Br, 15.0; Requires C, 59.70; H, 5.28; N, 16.07; Br, 15.28%.

EXAMPLE 36

(i) A mixture of 3-methyl-2-bromopyridine (15 g), 1,3-diaminopropane (37.3 g) and pyridine (10 ml) was heated under reflux for 3 hr. After stripping, the residue was treated with 2N sodium hydroxide and the product extracted into chloroform. The extract was dried, stripped and the residue distilled at reduced pressure to give 2-(3-aminopropylamino)-3-methylpyridine (6.94 g) bp 100° C., 0.09 mm Hg. (ii) Sodium hydride (1.11 g) was dissolved in DMSO (20 ml) at 70°-75° C. The solution was cooled and 2-(3-aminopropylamino)-3-methylpyridine (6.94 g) in DMSO (10 ml) added at room temperature. Methyl iodide (6.56g) in DMSO (20 ml) was added dropwise maintaining the temperature at 20°-25° C. After a further 1 hr, water (100 ml) was added and the mixture extracted with chloroform. The chloroform extract was washed with 2N hydrochloric acid. The pH of the acid extract was raised to 9.5 and extracted with chloroform. The pH was raised further to 14 and again extracted with chloroform. After stripping the final extract, the residue was taken back up in water and the product extracted out again with ether. After drying (K$_2$CO$_3$), stripping the ether extract gave 2-[N-(3-aminopropyl)-N-methylamino]-3-methylpyridine (4.46 g) as an oil which was used without further purification.

(iii) 2-[N-(3-aminopropyl)-N-methylamino]-3-methylpyridine (1.5 g) and 2-nitroamino-5-(6-methylpyrid-3-ylmethyl)pyrimid-4-one (1.46 g) were heated together under reflux in pyridine (10 ml) for 20 hr. The mixture was stripped and the residue triturated with water (pH adjusted to 7 with 6N hydrochloric acid) until a solid (2.1 g) was obtained. This was chromatographed (silica gel, 1–3% methanol/chloroform) and crystallised from acetone/water to give 2-[3-[N-methyl-N-(3-methylpyrid-2-yl)amino]-propylamino]-5-(6-methylpyrid-3-ylmethyl)pyrimid-4-one 1H$_2$O, 0.48 g (22%) mp 83°–85° C.

C$_{21}$H$_{26}$N$_6$O.1H$_2$O; Found C, 63.57; H, 7.09; N, 21.05; Requires C, 63.61; H, 7.12; N, 21.20%.

EXAMPLE 37

(i) Substituting 2-bromo-4-methylpyridine (25.8 g) for 2-bromo-3-methylpyridine and using the corresponding molar proportions of the other reagents in the method of Example 36(i) gave 2-(3-aminopropylamino)-4-methylpyridine (16.1 g), bp 120°–24° C.; 0.01–0.02 mm Hg. (ii) Substituting 2-(3-aminopropylamino)-4-methylpyridine (7.5 g) for 2-(3-aminopropylamino)-3-methylpyridine and using corresponding molar proportions of the other reagents in the method of Example 36(ii) gave 2-[N-(3-aminopropyl)-N-methylamino]-4-methylpryridine (3.53 g) as an oil. (iii) Substituting 2-[N-(3-aminopropyl)-N-methylamino]-4-methylpyridine (1.0 g) for 2-[N-(3-aminopropyl)-N-methyl amino]-3-methylpyridine and using corresponding molar proportions of the other reagents in method of Example 36(iii) gave 2-[3-[N-methyl-N-(4-methylpyrid-2-yl)amino] propylamino]-5-(6-methylpyrid-3-ylmethyl)pyrimid-4-one 1H$_2$O, 0.56 g (26%) mp indeterminate (from ethanol/water).

C$_{21}$H$_{26}$N$_6$O.1H$_2$O; Found C, 64.17; H, 7.17; N, 20.98; Requires C, 63.61; H, 7.12; N, 21.20%.

EXAMPLE 38

(i) Substituting 2-bromo-6-methylpyridine (25.8 g) for 2-bromo-3-methylpyridine and using the corresponding molar proportions of the other reagents in the method of Example 36(i) gave 2-(3-aminopropylamino)-6-methylpyridine (11.11 g) bp 121°–23° C.; 0.4mm Hg. (ii) Substituting 2-(3-aminopropylamino)-6-methylpyridine (7.5 g) for 2-(3-aminopropylamino)-3-methylpyridine and using corresponding molar proportions of the other reagents in the method of Example 36(ii) gave, after purification by HPLC (silica gel, 5% ammoniacal methanol/dichloromethane), 2-[N-(3-aminopropyl)-N-methylamino]-6-methylpyridine (1.72 g) as an oil. (iii) Substituting 2-[N-(3-aminopropyl)-N-methylamino]-6-methylpyridine (1.0 g) for 2-[N-(3-aminopropyl)-N-methyl amino]-3-methylpyridine and using the corresponding molar proportion of the other reagents in the method of Example 36(iii) gave 2-[3-[N-methyl-N-(6-methylpyrid-2-yl)amino]propylamino]-5-(6-methylpyrid-3-ylmethyl)pyrimid-4-one 1.6H$_2$O, 1.29 g (78%) mp softens 83°–86° C., melts 130°–36° C. (from ethanol/water).

C$_{21}$H$_{26}$N$_6$O.1.6H$_2$O; Found C, 61.76; H, 7.07; N, 20.88; Requires C, 61.92; H, 7.23; N, 20.63%.

EXAMPLE 39

2-[N-(3-aminopropyl)-N-benzylamino]pyridine (1 g) and 2-nitroamino-5-(5,6-dimethylpyrid-3-ylmethyl)-pyrimid-4-one (0.94 g) were heated together under reflux in pyridine (5 ml) for 20 hrs. After stripping the resulting solid was recrystallized from ethanol/water to give 2-[3-(N-benzyl-N-pyrid-2-ylamino)propylamino]-5-(5,6-dimethylpyrid-3-ylmethyl)pyrimid-4-one 0.75 H$_2$O, 0.61 g (38%) m.p. 95°–99° C.

C$_{27}$H$_{30}$N$_6$O 0.75 H$_2$O; Found C, 69.20; H, 6.68; N, 18.15; Requires C, 69.28; H, 6.78; N, 17.96%.

EXAMPLE 40

2-[N-(3-aminopropyl)-N-propylamino]pyridine (1.0 g) and 2-methylthio-5-(4-methoxybenzyl)pyrimid-4-one (0.88 g) were fused together on an oil bath at 160° C. for 2.5 hr. On cooling the residue was crystallized from ethanol/water to give a white solid which on recrystallization from acetone/water gave 2-[3-(N-propyl-N-pyrid-2-ylamino)propylamino]-5-(4-methoxybenzyl)-pyrimid-4-one 1 H$_2$O; 1.27 g (79%) m.p. indeterminate.

C$_{23}$H$_{29}$N$_5$O$_2$ H$_2$O; Found C, 65.23; H, 7.23; N, 16.66; Requires C, 64.92; H, 7.34; N, 16.46%.

EXAMPLE 41

2-[N-(3-aminopropyl)-N-propylamino]pyridine (1.09 g) and 2-methylthio-5-cyclohexylmethylpyrimid-4-one (0.9 g) were heated together under reflux in pyridine (2.5 ml) for 28 hr. After stripping, the residue was triturated with ether and crystallized twice from ethanol/water to give 2-[3-(N-propyl-N-pyrid-2-ylamino)-propylamino]-5-cyclohexylmethylpyrimid-4-one 0.5 H$_2$O, 1.14 g (78%) m.p. 103°–106° C.

C$_{22}$H$_{23}$N$_5$O 0.5 H$_2$O; Found C, 66.93; H, 8.89; N, 17.98; Requires C, 67.17; H, 8.74; N, 17.81%.

EXAMPLE 42

2-[N-(4-aminobutyl)-N-propylamino]pyridine (1.17 g) and 2-methylthio-5-cyclohexylmethylpyrimid-4-one (0.9 g) were heated together under reflux in pyridine (2.5 ml) for 28 hrs. After stripping, the residue was chromatographed (silica gel, dichloromethane/methanol 40:1) crystallized from ethanol/water and recrystallized from acetone/water to give 2-[4-(N-propyl-N-pyrid-2-ylamino)butylamino]-5-cyclohexylmethyl pyrimid-4-one 1.4 H$_2$O, 0.62 g (38%) m.p. 62°–64° C.

C$_{23}$H$_{35}$N$_5$O 1.4 H$_2$O; Found C, 65.74; H, 8.95; N, 16.65; Requires C, 65.46; H, 9.01; N, 16.60%.

EXAMPLE 43

(i) Substituting n-butyl bromide (8.3 g) for n-propyl iodide and using the corresponding molar proportions of the other reagents in the method of example 30(i) gave 2-[N-(4-aminobutyl)-N-butylamino]pyridine (6.5 g) as an oil. (ii) 2-[N-(4-aminobutyl)-N-butylamino]pyridine (1.24 g) and 2-methylthio-5-(4-chlorobenzyl)-pyrimid-4-one (1.0 g) were heated together under reflux in pyridine (2.5 ml) for 28 hr. After stripping, the residue was triturated with wet ether and recrystallized from isopropanol/water to give 2-[4-(N-butyl-N-pyrid-2-ylamino)butylamino]-5-(4-chlorobenzyl)pyrimid-4-one 1 H$_2$O, 1.10 g (64%) m.p. 80°–82° C.

C$_{24}$H$_{30}$ClN$_5$O H$_2$O; Found C, 62.80; H, 7.02; N, 15.23; Cl, 7.57; Requires C, 62.94; H, 7.04; N, 15.29; Cl, 7.74%.

EXAMPLE 44

(i) Substituting ethyl iodide (10.31 g) for n-propyl iodide and using the corresponding molar proportions of the other reagents in the method of example 15(i) gave 2-[N-(3-aminopropyl)-N-ethylamino]pyridine (2.32 g) as an oil. (ii) 2-[N-(3-aminopropyl)-N-ethylamino]pyridine (1.0 g) and 2-methylthio-5-(4-chlorobenzyl)pyrimid-4-one (0.99 g) were heated together under reflux in pyridine (2.5 ml) for 28 hr. After stripping the residue was crystallized from ethanol and recrystallized from ethanol/water to give 2-[3-(N-ethyl-N-pyrid-2-ylamino)propylamino]-5-(4-chlorobenzyl)-pyrimid-4-one 0.9 H$_2$O, 1.23 g (79%) m.p. 86°–89° C.

C$_{21}$H$_{24}$ClN$_5$O 0.9 H$_2$O; Found C, 61.01; H, 6.20; N, 17.22; Cl, 8.69; Requires C, 60.98; H, 6.27; N, 16.93; Cl, 8.57%.

EXAMPLE 45

(i) Substituting n-butyl bromide (9.06 g) for n-propyl iodide and using the corresponding molar proportions of the other reagents in the method of example 15(i) gave 2-[N-(3-aminopropyl)-N-butylamino]pyridine (9.07 g) as an oil. (ii) 2-[N-(3-aminopropyl)-N-butylamino]pyridine (1.0 g) and 2-methylthio-5-(4-chlorobenzyl)pyrimid-4-one (0.86 g) were heated together under reflux in pyridine (2.5 ml) for 28 hr. After stripping the residue was triturated with ether and recrystallized from ethanol/water to give 2-[3-(N-butyl-N-pyrid-2-ylamino)propylamino]-5-(4-chlorobenzyl)-pyrimid-4-one 1 H$_2$O, 1.06 g (74%) m.p. 74°–77° C.

C$_{23}$H$_{28}$ClN$_5$O H$_2$O; Found C, 62.18; H, 6.74; N, 15.90; Cl, 7.79; Requires C, 62.22; H, 6.81; N, 15.78; Cl, 7.99%.

EXAMPLE 46

2-[N-(4-aminobutyl)-N-propylamino]pyridine (0.9 g) and 2-nitroamino-5-pyrid-4-ylmethylpyrimid-4-one (0.72 g) were heated together under reflux in pyridine (2.5 ml) for 21 hr. After stripping the residue was taken up in water, basified, and extracted with ether. The aqueous was acidified (pH 6.5), extracted with dichloromethane and stripped to give an oil which was crystallized from ethanol/water to give 2-[4-(N-propyl-N-pyrid-2-ylamino)butylamino]-5-pyrid-4-ylmethylpyrimid-4-one 1.2 H$_2$O; 0.45 g (38%) m.p. 58°–60° C.

C$_{22}$H$_{28}$N$_6$O 1.2 H$_2$O; Found C, 63.56; H, 7.31; N, 20.03; Requires C, 63.75; H, 7.37; N, 20.28%.

EXAMPLE 47

2-[N-(4-aminobutyl)-N-propylamino]pyridine (1.18 g) and 2-nitroamino-5-(N-oxo-pyrid-4-ylmethyl)pyrimid-4-one (1.0 g) were heated together under reflux in pyridine (2.5 ml) for 7 hrs. After stripping, the residue was chromatographed (silica gel, dichloromethane/methanolic ammonia 20:1) and crystallized from isopropanol/water to give 2-[4-(N-propyl-N-pyrid-2-ylamino)butylamino]-5-(N-oxo-pyrid-4-ylmethyl)-pyrimid-4-one 1 H$_2$O, 0.84 g (52%) m.p. 70°–73° C.

C$_{22}$H$_{28}$N$_6$O$_2$ H$_2$O; Found C, 61.74; H, 6.81; N, 19.58; Requires C, 61.95; H, 7.09; N, 19.71%.

EXAMPLE 48

2-[N-(3-aminopropyl)-N-benzylamino)pyridine (1.0 g) and 2-nitroamino-5-(pyrid-4-ylmethyl)pyrimid-4-one (0.68 g) were heated together under reflux in pyridine (2.5 ml) for 23 hr. After stripping the residue was twice crystallized from ethanol/water to give 2-[3-(N-benzyl-N-pyrid-2-ylamino)propylamino]-5-pyrid-4-ylmethylpyrimid-4-one 1.6 H$_2$O, 0.86 g (68%) m.p. 87°–89° C.

C$_{25}$H$_{26}$N$_6$O 1.6 H$_2$O; Found C, 66.12; H, 6.05; N, 18.33; Requires C, 65.82; H, 6.47; N, 18.42%.

EXAMPLE 49

2-[N-(4-aminobutyl)-N-propylamino]pyridine (2.24 g) and 2-nitroamino-5-(2-methoxypyrid-4-ylmethyl)-pyrimid-4-one (2.00 g) was heated under reflux for 23 hrs. After stripping, the residue was chromatographed (silica gel, dichloromethane/methanol 25:1) and treated with maleic acid to give, after crystallization from ethanol/diethyl ether, 2-[4-(N-propyl-N-pyrid-2-ylamino)butylamino]-5-(2-methoxypyrid-4-ylmethyl)-pyrimid-4-one dimaleate, 0.98 g (21%) m.p. 145°–147° C.

C$_{23}$H$_{30}$N$_6$O$_2$ 2C$_4$H$_4$O$_4$; Found C, 56.65; H, 5.89; N, 12.83; Requires C, 56,87; H, 5.85; N, 12.84%.

EXAMPLE 50

2-[4-(N-propyl-N-pyrid-2-ylamino)butylamino]-5-(2-methoxy pyrid-4-ylmethyl)pyrimid-4-one (1.8 g) in ethanol (50 ml) saturated with hydrogen chloride was heated under reflux for 40 hrs. After stripping, the residue was triturated with ether. The residue was taken up in water, basified and extracted with ether, acidified to neutral pH and extracted with chloroform. After stripping, the residue was crystallized from methanol to give 2-[4-(N-propyl-N-pyrid-2-ylamino)butylamino]-5-(2-hydroxypyrid-4-ylmethyl)pyrimid-4-one 1.4 H$_2$O, 0.80 g (43%) m.p. 138°–140° C.

C$_{22}$H$_{28}$N$_6$O$_2$ 1.4 H$_2$O; Found C, 60.75; H, 6.47; N, 19.39; Requires C, 61.00; H, 7.15; N, 19.40%.

EXAMPLE 51

2-[N-(4-aminobutyl)-N-propylamino]pyridine (1.24 g) and 2-methylthio-5-(4-fluorobenzyl)pyrimid-4-one (1.25 g) were fused together on an oil bath at 160° C. for 2.5 hr. On cooling the residue was crystallized from ethanol/water to give 2-[4-(N-propyl-N-pyrid-2-ylamino)butylamino]-5-(4-fluorobenzyl)pyrimid-4-one 1.25H$_2$O, 0.56 g (26%) m.p. indeterminate.

C$_{23}$H$_{28}$FN$_5$O 1.25 H$_2$O; Found C, 63.97; H, 7.01; N, 16.22; Requires C, 63.94; H, 7.12; N, 16.21%;

What is claimed is:

1. A compound of formula (1):

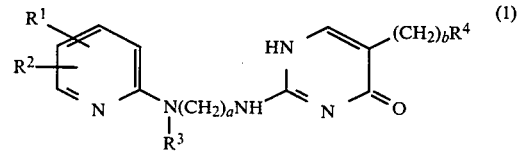

or a pharmaceutically acceptable salt thereof where
$R_1$ and $R^2$ are the same or different and are hydrogen, C$_{1-6}$ alkyl C$_{1-6}$ alkoxy, or halogen;
$R^3$ is C$_{1-6}$ alkyl, C$_{3-8}$ cycloalkyl C$_{1-6}$ alkyl, optionally substituted phenyl or optionally substituted phenyl C$_{1-6}$ alkyl, where the optional substituents are one or two C$_{1-6}$ alkyl, C$_{1-6}$ alkoxy, halogen, or hydroxy groups; or is an optionally substituted pyridyl or optionally substituted pyridyl C$_{1-6}$ alkyl where the optional substituents are one or two C$_{1-6}$ alkyl or C$_{1-6}$ alkoxy groups or halogen atoms;
a is from 2 to 4
b is from 1 to 6

$R^4$ is hydrogen, optionally substituted phenyl where the optional substituents are one or two $C_{1-6}$ alkyl, $C_{1-6}$ alkoxy, or hydroxy groups or halogen atoms one nitro group, or a methylenedioxy group, or is an optionally substituted pyridyl group where the optional substituents are one or two $C_{1-6}$ alkyl $C_{1-6}$ alkoxy groups or halogen atoms; or is a $C_{3-8}$ cycloalkyl group, or is N-oxo-3-pyridyl; N-oxo-6-methyl-3-pyridyl; 6-hydroxymethyl-3-pyridyl; N-oxo-4,6-dimethyl-3-pyridyl; 6-hydroxymethyl-4-methyl-3-pyridyl; N-oxo-5,6-dimethyl-3-pyridyl; 6-hydroxymethyl-5-methyl-3-pyridyl; or N-oxo-4-pyridyl, or is a pyridone group in which the nitrogen atom is optionally substituted with $C_{1-6}$ alkyl.

2. A compound according to claim 1 where a is 3 or 4.

3. A compound according to claim 1 where $R^1$ and $R^2$ are both hydrogen.

4. A compound according to claim 1 where $R^3$ is $C_{1-6}$ alkyl.

5. A compound according to claim 3 where $R^3$ is methyl or propyl.

6. A compound according to claim 1 where $R^3$ is phenyl.

7. A compound according to claim 1 where $R^3$ is optionally substituted phenyl $C_{1-6}$ alkyl.

8. A compound according to claim 7 where $R^3$ is benzyl, 3-chlorobenzyl, 4-chlorobenzyl or 4-methoxybenzyl.

9. A compound according to claim 1 where b is 1.

10. A compound according to claim 1 where $R^4$ is optionally substituted phenyl.

11. A compound according to claim 10 where $R^4$ is phenyl, 2-chlorophenyl, 3-chlorophenyl, 4-chlorophenyl, 3,4-dichlorophenyl, 2-bromophenyl, 3-bromophenyl, 4-bromophenyl, 4-fluorophenyl, 4-methylphenyl, 4-methoxyphenyl, 4-hydroxyphenyl, 3-nitro-4-hydroxyphenyl and 3,4-benzodioxolyl.

12. A compound according to claim 1 where $R^4$ is optionally substituted pyridyl.

13. A compound according to claim 12 where $R^4$ is 6-methyl-2-pyridyl.

14. A pharmaceutical composition having histamine $H_1$-antagonist activity comprising an effective amount of a compound according to claim 1 and a pharmaceutically acceptable carrier.

15. A method of blocking histamine $H_1$-receptors which comprises administering to a subject an effective amount to block said receptors of a compound according to claim 1.

* * * * *